United States Patent
Iskra

Patent Number: 5,271,987
Date of Patent: Dec. 21, 1993

[54] UNITARY ABSORBENT STRUCTURE

[75] Inventor: Michael J. Iskra, Kent, Wash.

[73] Assignee: Weyerhaeuser Company, Tacoma, Wash.

[21] Appl. No.: 821,245

[22] Filed: Jan. 10, 1992

Related U.S. Application Data

[63] Continuation of Ser. No. 339,158, Apr. 17, 1989, abandoned.

[51] Int. Cl.⁵ .............................................. B32B 23/02
[52] U.S. Cl. ..................................... 428/192; 428/283; 428/284; 428/286; 428/296; 428/198; 428/373; 428/913; 604/367; 604/368
[58] Field of Search ................ 428/224, 236, 237, 240, 428/246, 192, 286, 373, 913; 418/283, 296, 284, 198; 604/367, 368

[56] References Cited

U.S. PATENT DOCUMENTS

| | | | |
|---|---|---|---|
| 3,901,240 | 8/1975 | Hoey | 428/236 |
| 4,219,024 | 8/1980 | Patience et al. | 128/287 |
| 4,542,060 | 9/1985 | Yoshida et al. | 428/284 |
| 4,573,988 | 3/1986 | Pieniak et al. | 604/379 |
| 4,605,402 | 8/1986 | Iskra | 604/368 |
| 4,737,404 | 4/1988 | Jackson | 428/284 |
| 4,994,053 | 2/1991 | Lang | 428/117 |

FOREIGN PATENT DOCUMENTS 0108637 5/1984 European Pat. Off. .
0163287 12/1985 European Pat. Off. .

Primary Examiner—James J. Bell
Attorney, Agent, or Firm—Dressler, Goldsmith, Shore & Milnamow, Ltd.

[57] ABSTRACT

A unitary absorbent structure is provided with an absorbent pad that includes at least an absorbing layer of absorbent material for absorbing and holding body fluids. A facing layer of body fluid-pervious material is placed the adjacent the absorbing pad. The facing layer and absorbing layer are positioned in face-to-face contact with the contacting faces bonded together over substantially the entire contact area. A fluid-distributing layer may be adhered to one surface of the absorbing layer. A backing sheet may be disposed adjacent the absorbent pad, and edge portions of the backing sheet may be wrapped around the edges of the structure and heat sealed to the facing layer.

14 Claims, 1 Drawing Sheet

UNITARY ABSORBENT STRUCTURE

This application is a continuation of application Ser. No. 07/339,158, filed Apr. 17, 1989, now abandoned.

TECHNICAL FIELD

This invention relates to a new and improved absorbent structure and to a method for making the structure. The improved structure is particularly well-suited for use with absorbent composites incorporating superabsorbent materials. The absorbent structure of the present invention may be incorporated in, among other things, disposable diapers, sanitary napkins, wound dressings, bandages, incontinent pads, and the like.

BACKGROUND OF THE INVENTION AND TECHNICAL PROBLEMS POSED BY THE PRIOR ART

Absorbent structures have been developed or proposed for use in absorbent products, such as diapers and sanitary napkins. Such structures typically include multiple layers of materials such as a moisture-pervious facing material, an absorbing material, a wicking or fluid-distributing material, and a moisture-impervious backing material.

When various layers are placed together in face-to-face relationship in such structures, means must be provided for maintaining a desired relationship and for maintaining the structural integrity of the product. In some prior art structures that have been developed or proposed, the outermost or exterior layer on one side of the structure is provided with lateral extensions which are attached by glueing or heat sealing to lateral extensions of the outermost or exterior layer on the other side of the product. The internal layers are thus contained within this envelope formed by the two exterior layers. However, when such structures are used, the internal layers may tend to move and bunch up. Manipulations of the structure during normal use may tend to cause relative displacement or distortions between some of the layers.

To some extent, the undesired relative displacement or bunching of the layers can be reduced by glueing an exterior layer to an adjacent inner layer. However, this necessarily results in an additional manufacturing step. It also requires materials and layer designs which accommodate such glueing, and it does not necessarily reduce displacement between the interior layers.

Accordingly, it would be desirable to provide a structure having a unitary construction that eliminates or substantially reduces bunching or relative displacement between layers.

It would be beneficial to provide a multi-layer absorbent structure which could be fabricated as a unitary, and easily handled, component for use in a variety of products, including disposable diapers and sanitary napkins.

It would also be desirable to provide a unitary absorbent structure having multiple layers wherein intimate contact between the layers is established.

Additionally, it would be advantageous if such an improved absorbent structure could be provided with a moisture-impervious barrier sheet that could be attached to the structure in a way so as to eliminate glueing.

SUMMARY OF THE INVENTION

A unitary absorbent structure is provided with an absorbent pad that includes at least an absorbing layer of absorbent material for absorbing and holding body fluids.

The structure includes a facing layer of body fluid-pervious material adjacent the absorbing pad.

The facing layer and absorbing layer are positioned in face-to-face contact with the contacting faces bonded together over substantially the entire contact area.

In a preferred embodiment of the structure, the facing layer comprises heat-fusible fibers. The absorbing layer includes absorbent material comprising a heat-fusible, fibrous web with particles of superabsorbent material disposed intermittently throughout the fibrous web.

Also, in the preferred embodiment, a fluid-distributing layer is intimately attached to the absorbing layer. The fluid distributing layer comprises hydrophilic particles or fibers sufficiently closely spaced to promote rapid wicking of liquid along the plane of the fluid-distributing layer.

Preferably, the structure further includes a backing sheet comprising a body fluid-impervious, heat-fusible material positioned in face-to-face relationship with the absorbent pad. Edge portions of the backing sheet are wrapped around the edges of the bonded-together absorbent pad and facing layer, and the edge portions are heat sealed to margins of the facing layer.

A method for fabricating the absorbent structure comprises the steps of forming an absorbent pad which includes at least an absorbing layer having two oppositely facing side surfaces and having the capability for absorbing and holding body fluids.

A facing layer of body fluid-pervious material is provided and is placed adjacent one side of the absorbing layer in face-to-face contact. The facing and absorbing layers are bonded together over substantially the entire contact area.

In a preferred form of the method, the facing layer and absorbing layer are thermally bonded together by elevating the temperatures of the layers in an oven while the layers are in face-to-face contact.

Further, the absorbing layer is preferably given superabsorbent characteristics by interspersing therein an absorbent material. The superabsorbent material is preferably applied to one side of the absorbing layer by means of spraying the superabsorbent material onto the absorbing layer or by coating the absorbing layer with the superabsorbent material from a kiss roll.

Further, in a preferred form of the method of fabricating the structure, a fluid distributing layer, which may be formed from cellulosic fibers, is pressed onto the coated side of the absorbing layer.

According to another aspect of the method of the present invention, a backing sheet may be uniquely incorporated into the absorbing structure. The absorbing structure is first formed with at least an absorbent pad for absorbing and holding body fluids. The absorbent pad has two oppositely facing side surfaces. The pad includes an absorbing layer which may or may not have superabsorbent material interspersed therein and which may or may not include a fluid-distributing layer.

A facing layer of a heat-fusible, body fluid-pervious material is attached to one side of the absorbent pad. In a preferred form of the process, wherein superabsorbent material is interspersed in the absorbent pad, the facing layer is initially fabricated from a heat-fusible, body fluid-pervious material and is attached by thermal bonding to one side surface of the absorbent pad before the superabsorbent material is interspersed in the absorbent pad.

In any case, regardless of whether the absorbent pad does or does not include superabsorbent material, a backing sheet of body fluid-impervious, heat-fusible material is placed adjacent a side surface of the absorbent pad. Laterally extending edge portions of the backing sheet are wrapped around edges of the absorbent pad and the attached facing layer. Then the backing sheet edge portions are heat sealed to margins of the facing layer to form a unitary structure.

Numerous other advantages and features of the present invention will become readily apparent from the following detailed description of the invention, from the claims, and from the accompanying drawings.

BRIEF DESCRIPTION OF THE DRAWINGS

In the accompanying drawings forming part of the specification, in which like numerals are employed to designate like parts throughout the same.

DESCRIPTION OF THE PREFERRED EMBODIMENTS

While this invention is susceptible of embodiment in many different forms, this specification and the accompanying drawings discuss only some specific forms as examples of the use of the invention. The invention is not intended to be limited to the embodiments so described, and the scope of the invention will be pointed out in the appended claims.

Figure 1:
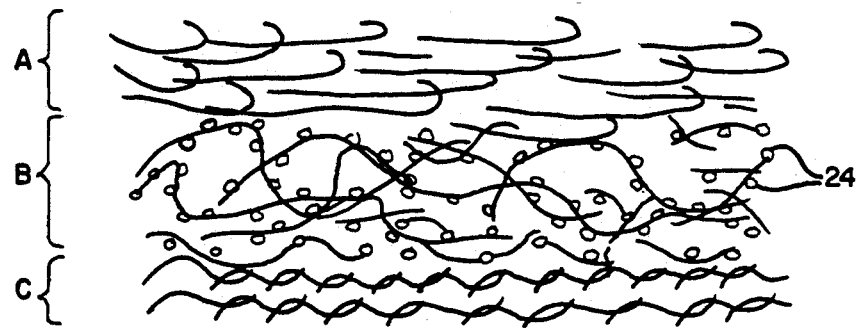
FIG. 1 is a greatly enlarged, diagrammatic, cross-sectional view (not to scale) of a unitary absorbing structure of the present invention.
Figure 2:
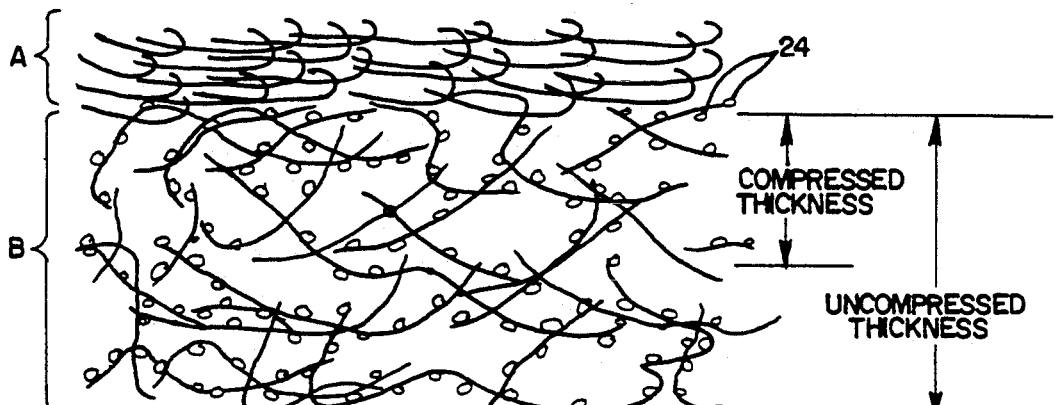
FIG. 2 is a view similar to FIG. 1 of a second embodiment in the form of an intermediate unitary absorbent structure shown in an uncompressed state.
Figure 3:
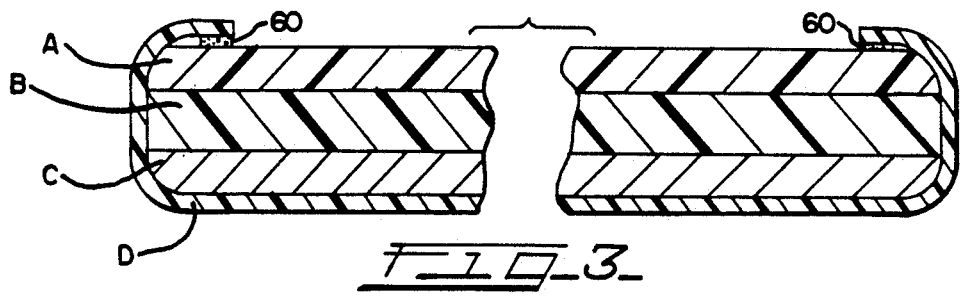
FIG. 3 is a greatly enlarged, fragmentary, cross-sectional view (not to scale) of a third embodiment of a unitary absorbing structure of the present invention.

FIG. 1 represents a diagrammatic, cross-sectional view of one embodiment of the unitary absorbent structure according to the principles of the present invention. The structure includes layers A, B, and C, which are described in detail hereinafter. An intermediate unitary absorbent structure, which may be regarded as another embodiment of the present invention, is illustrated in FIG. 2 and includes only layers A and B. A third embodiment of the structure illustrated in FIG. 3 is shown as a completed product, such as in the form of a disposable diaper, including the layers A, B, and C, as well as an additional layer D.

The unitary absorbent structure illustrated in FIG. 1 includes a facing layer A consisting of a material that is moisture-pervious or fluid-pervious. It is disposed adjacent an absorbent pad which may comprise the remaining layers B and C.

Layer B is an absorbing layer of absorbent material for absorbing and holding body fluids. The absorbing layer B is in face-to-face contact with the facing layer A, and the contacting faces of layers A and B are bonded together over substantially the entire contact area.

Layer C is a fluid-distributing layer (sometimes referred to as a wicking layer) that is attached to the absorbing layer B. The layer C may also be attached to layer B with or without the use of an additional binder layer.

The facing layer A, in the preferred form, comprises heat-fusible fibers, and the absorbing layer B also preferably includes heat-fusible fibers in the form of a fibrous web. The facing layer A and the absorbing layer B can thus be thermally bonded together by elevating the temperatures of the layers in an oven while the layers are in face-to-face contact.

The facing layer A may be fabricated from a conventional heat-fusible fiber such as that sold in the United States of America under the trade name Bico by BASF Company, New York, U.S.A. The facing layer may include a conventional heat-fusible conjugate structure having a core consisting of a first material surrounded by a jacket consisting of a second material.

The absorbing layer B may be provided as a conventional fibrous web material such as that sold in the United States under the designation T375W by DuPont Company, Wilmington, Del., U.S.A.

Typically, the absorbing layer B has a lower density than the facing layer A. U.S. Pat. No. 4,573,988 describes a variety of materials and fibers which may be used to form the absorbing layer B and describes processes for forming the absorbing layer B as a web of fibers.

The absorbing layer B may also be provided with particles 24 of superabsorbent material interspersed or disposed intermittently throughout the fibrous web. Suitable superabsorbent materials and processes for applying superabsorbent materials along with water are described in detail in the above-discussed U.S. Pat. No. 4,575,988.

The fluid distributing layer C may be of a conventional composition comprising substantially uniformly disposed, hydrophilic particles or fibers selected from the group consisting of cellulosic fibers, peat moss, rayon fibers, acrylic fibers, and mixtures thereof. Particles or fibers of comminuted wood pulp (sometimes referred to as wood fluff) are particularly preferred for low cost. Preferably, the hydrophilic particles, regardless of their composition, are sufficiently closely spaced (i.e., densified) to promote rapid wicking of liquid along the plane of the fluid distributing layer C. Materials which may be used to form the wicking or fluid distributing layer C, and processes for forming such a layer, are described in the above-discussed U.S. Pat. No. 4,573,988.

The multi-layered structure of FIG. 1 may be incorporated in a product illustrated in FIG. 3. In FIG. 3, the various above-described layers A, B, and C are shown as cross-sectioned layers to simplify the illustration. A backing layer or sheet D is provided in the form of a body fluid-impervious, heat-fusible material. The backing layer D may comprise suitable moisture-impervious material such as polyethylene or polyethylene terephthalate having a thickness on the order of 0.001 inches. The backing sheet D is positioned in face-to-face relationship with the absorbent pad structure (consisting of the attached layers B and C).

Edge portions of the backing sheet D are wrapped around the edges of the absorbent pad layers B and C and around the attached facing layer A. The backing sheet edge portions are positioned on top of the margins of the facing layer A, and the backing sheet edge portions are heat sealed, as at 60, to the margins of the facing layer A. Of course, the facing layer A must be formed from a heat-fusible material in this embodiment.

It is seen that the embodiment illustrated in FIG. 3 has a structure that is wrapped, except for an exposed surface of the facing layer, by the fluid-impervious backing sheet D which is intimately attached, as by heat sealing, to the facing layer A. No glue or other adhesive is then required to attach the backing sheet D to any of the other layers.

According to a preferred method of the present invention, the unitary absorbent structure may be fabricated by first carding and combining the absorbing layer B with the facing layer A. If the facing layer A consists of the material sold under the above-discussed trade name BICO and if the absorbing layer B consists of the material sold under the above-discussed trade name T375W, then the layers are formed in the illustrated face-to-face relationship wherein the initial thickness of the absorbing layer B is typically substantially greater than the thickness of the facing layer A. This thickness relationship is illustrated in FIG. 2.

The facing layer A and absorbing layer B are then heated to an elevated temperature, such as in a thermal oven, so as to intimately bond them together.

Next, the bonded-together structure of layers A and B is oriented to permit the application of a superabsorbent material (particles 24) to the absorbing layer B. The superabsorbent material 24 may be applied to the exposed side of the absorbing layer B by means of a kiss roll or may be sprayed onto the exposed side.

Processes for applying superabsorbent material to a fibrous web absorbing layer B are described in detail in the above-discussed U.S. Pat. No. 4,573,988. Typically, after application of the superabsorbent material 2A, the intermediate structure, which is illustrated in FIG. 2, is subjected to compression for a predetermined period of time. Upon release of the pressure, the absorbing layer B of the structure remains substantially compressed.

Instead of compressing the absorbent structure illustrated in FIG. 2 immediately after adding the superabsorbent material 24, the compressing step may be postponed. The fluid distributing layer C may be first attached to the exposed surface of the absorbing layer B.

Various processes for incorporating a fluid distributing layer C in the structure are described in the above-discussed U.S. Pat. No. 4,573,988. The process for applying the fluid distributing layer C onto the exposed surface of the absorbing layer B can include compressing all of the layers A, B, and C together for a predetermined time.

Upon release of the pressure, the absorbing layer B and the fluid distributing layer C remain substantially compressed, whereas the facing layer A may return to substantially the original, uncompressed thickness. The resulting structure is shown in the FIG. 1 embodiment. This resulting embodiment may be characterized as an integral or unitary absorbent structure in which the adjacent layers of the multiple layer structure are intimately attached in face-to-face relationship.

The unitary structure fabricated according to the method of the present invention, and as illustrated in FIG. 1, may be readily incorporated in various products, including disposable diapers and sanitary napkins. Further, according to another aspect of the method of the present invention, a fluid-impervious backing sheet D may be then placed adjacent the absorbent structure as illustrated in FIG. 3 to form a modified absorbent structure.

In particular, the backing sheet D is provided with lateral edge portions which extend beyond the edges of the layers (layers A and B if no fluid distributing layer C is employed, or layers A, B, and C if a fluid distributing layer is employed). The backing sheet edge portions are wrapped around the layer edges and are positioned on top of the lateral margins of the facing layer A. If the backing sheet D and facing layer A consist of heat-fusible materials, then the backing sheet edge portions can then be heat sealed, as at 60, to the margins of the facing layer A.

Thus, it is seen the present invention provides a unitary absorbent structure and a method for fabricating such an absorbent structure. The absorbent structure includes layers which are intimately attached to prevent relative lateral displacement or bunching. A backing sheet can be provided and heat sealed to the facing layer so as to eliminate the need for glue or adhesive.

It will be readily observed from the foregoing detailed description, and from the illustrated embodiments thereof that numerous variations and modifications may be effected without departing from the true spirit and scope of the novel concepts of the invention.

What is claimed is:

1. A unitary absorbent structure comprising:
    an absorbing layer of material for absorbing and holding body fluids, said absorbing layer having two oppositely facing surfaces defined within peripheral edges of said absorbing layer;
    a facing layer of body fluid-pervious material adjacent said absorbing layer, said facing layer having two oppositely facing surfaces defined within peripheral edges of said facing layer;
    said facing layer and said absorbing layer being positioned with one of said absorbing layer surfaces confronting one of said facing surfaces in face-to-face contact with the contacting surfaces being thermally bonded together within said peripheral edges to minimize relative displacement and distortions whereby liquid transport from said facing layer into said absorbing layer is facilitated; and
    a superabsorbent material applied to said absorbing layer of said absorbent material,
    said contacting surfaces of said facing layer and said absorbing layer being thermally bonded by bonding of said facing layer to fibers of said material of said absorbing layer which said fibers do not have superabsorbent material applied thereto.

2. A unitary absorbent structure in accordance with claim 1 in which said absorbing layer comprises a fibrous web.

3. The structure in accordance with claim 2 in which said absorbing layer includes a plurality of particles of superabsorbent material disposed intermittently throughout said fibrous web.

4. The structure in accordance with claim 2 in which said absorbing layer further includes a fluid distributing layer intimately attached to said absorbing layer opposite said facing layer.

5. The structure in accordance with claim 4
    in which said fluid distributing layer includes hydrophilic particles selected from the group consisting of cellulosic fibers, peat moss, rayon fibers, acrylic fibers, and mixtures thereof; and
    in which said absorbing layer has a substantially reduced thickness as a result
    a superabsorbent material applied to said absorbing layer of said absorbent material,
    said contacting surfaces of said facing layer and said absorbing layer being thermally bonded by bonding of said facing layer to fibers of said material of said absorbing layer which said fibers do not have superabsorbent material applied thereto.

6. The structure in accordance with claim 4 in which said fluid distributing layer comprises substantially uniformly disposed, hydrophilic particles selected from the group consisting of cellulosic fibers, peat moss, rayon fibers, acrylic fibers, and mixtures thereof, said hydrophilic particles being sufficiently closely spaced to promote rapid wicking of liquid along the plane of said fluid distributing layer.

7. The structure in accordance with claim 1 in which said absorbing layer includes a heat-fusible material and said facing layer includes a heat-fusible material.

8. The structure in accordance with claim 1 in which said facing layer is a nonwoven fabric.

9. The structure in accordance with claim 1
in which said facing layer comprises heat-fusible fibers; and
in which said structure further includes a backing sheet comprising a body fluid-impervious, heat-fusible material positioned in face-to-face relationship with said absorbing layer and having edge portions wrapping around the edges of said absorbing layer and said facing layer with said backing sheet edge portions being heat sealed to margins of said facing layer.

10. The structure in accordance with claim 9 in which said backing sheet is polyethylene.

11. The structure in accordance with claim 1 in which said facing layer comprises a conjugate structure having a core consisting of a first material surrounded by a jacket consisting of a second material.

12. The structure in accordance with claim 1 in which said contacting surfaces are thermally bonded together over substantially the entire contact area.

13. The structure in accordance with claim 1 in which the peripheral edges of said facing layer and said absorbing layer are in registry.

14. The structure in accordance with claim 1, in which said superabsorbent material is applied to said absorbing layer of absorbent material after said facing layer and said absorbing layer have been bonded together.

* * * * *